United States Patent [19]
Carlson et al.

[11] Patent Number: 5,569,254
[45] Date of Patent: Oct. 29, 1996

[54] SURGICAL RESECTION TOOL HAVING AN IRRIGATION, LIGHTING, SUCTION AND VISION ATTACHMENT

[75] Inventors: Glenn T. Carlson; William J. Vaughn, both of Fort Worth; Ray E. Umber, Arlington, all of Tex.

[73] Assignee: Midas Rex Pneumatic Tools, Inc., Fort Worth, Tex.

[21] Appl. No.: 420,661

[22] Filed: Apr. 12, 1995

[51] Int. Cl.⁶ ................................................ A61B 17/00
[52] U.S. Cl. ........................... 606/79; 606/80; 606/170; 128/751; 128/755; 600/101; 600/109
[58] Field of Search ................................. 600/101, 109, 600/113, 121, 125, 127, 130, 137, 138, 182; 604/22; 606/79, 80, 167, 170, 171, 159; 128/751, 755; 279/42, 48

[56] References Cited

U.S. PATENT DOCUMENTS

| | | |
|---|---|---|
| 3,128,768 | 11/1961 | Geistauts .................... 128/305 |
| 3,844,272 | 10/1974 | Banko . |
| 4,330,274 | 5/1982 | Friedman et al. . |
| 4,517,977 | 5/1985 | Frost . |
| 4,598,710 | 7/1986 | Kleinberg et al. . |
| 4,601,290 | 7/1986 | Effron et al. . |
| 4,834,729 | 5/1989 | Sjostrom . |
| 4,850,354 | 7/1989 | McGurk-Burleson et al. . |
| 4,887,599 | 12/1989 | Muller . |
| 4,983,179 | 1/1991 | Sjostrom . |
| 5,003,434 | 3/1991 | Gonser et al. . |
| 5,312,399 | 5/1994 | Hakky et al. ................ 606/170 |

*Primary Examiner*—Michael Powell Buiz
*Assistant Examiner*—Mark S. Leonardo
*Attorney, Agent, or Firm*—James E. Bradley

[57] ABSTRACT

A surgical tool for resecting bone includes a pneumatic motor to which a bearing tube is secured for rotatably supporting a resecting tool. The bearing tube is eccentrically disposed within an attachment tube, with a flow channel defined between an interior of the attachment tube and an exterior of the bearing tube. Irrigation fluid is passed through the flow channel to maintain a constant flow of irrigation fluid about a cutting end of the resecting tool. Optical fibers extend within the attachment tube for passing light to lenses disposed at the specimen end of the attachment tube for providing illumination. At least one optical fiber extends from a lens at the specimen end, through the attachment tube, and to an optical viewer for providing a means for inspecting the bone being resected. The attachment tube is slidably adjustable along the bearing tube for selecting a distance between the specimen end of the attachment tube and the cutting end of the resecting tool.

26 Claims, 2 Drawing Sheets

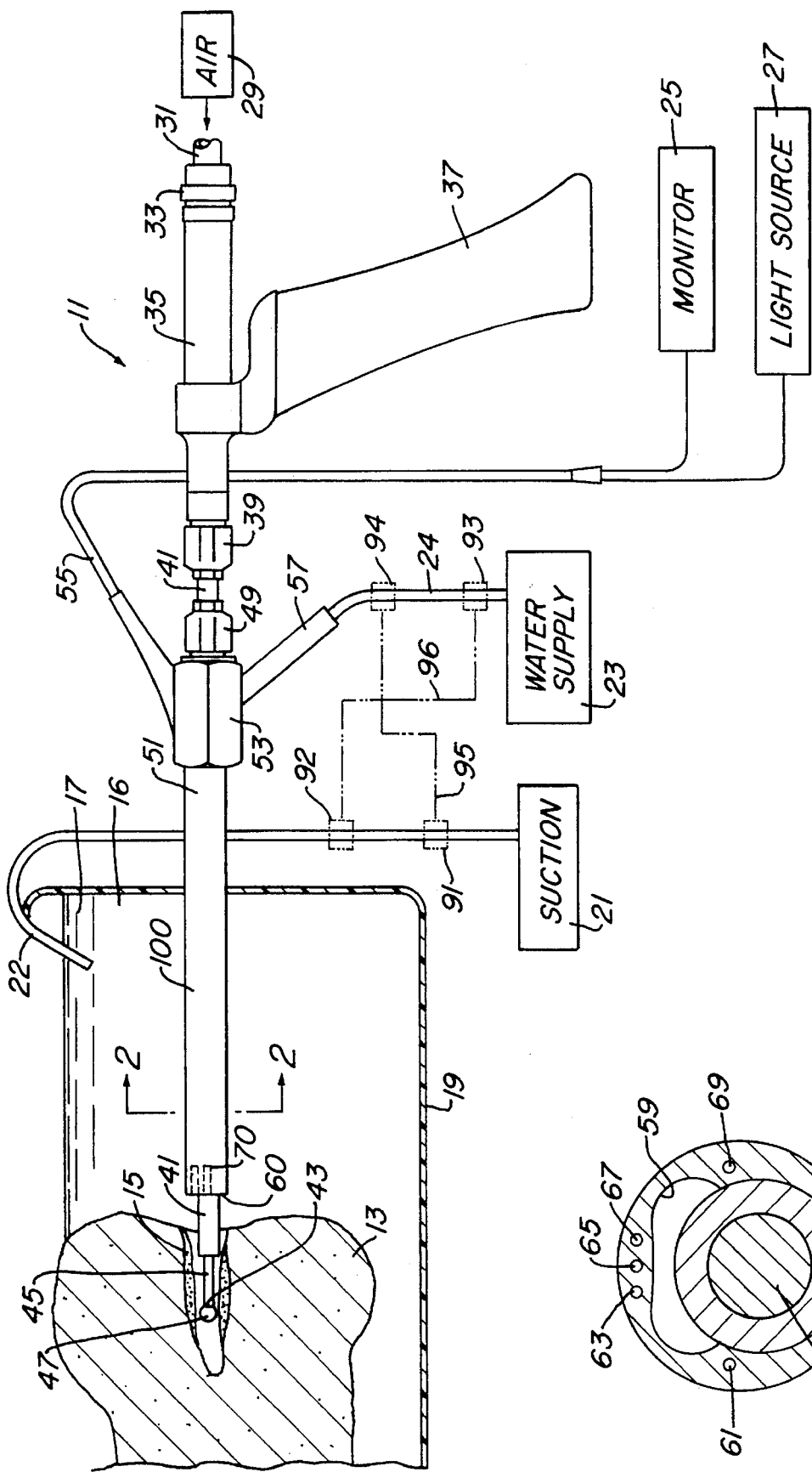

SURGICAL RESECTION TOOL HAVING AN IRRIGATION, LIGHTING, SUCTION AND VISION ATTACHMENT

BACKGROUND OF THE INVENTION

1. Field of the Invention

The present invention relates to surgical tools for orthopedic operations, and in particular to motorized surgical tools for resecting bones.

2. Description of the Prior Art

Surgical tools have been used for resecting bone, such as in hip replacement operations. Typically a hole is drilled within a bone, such as a femur, for placement of a pin for securing members together. In some circumstances, a second surgery may be required for further orthopedic restorations, often requiring replacement of a joined member, such as a donor bone or artificial member. It is desirable that prior adhesives for securing the previously joined member to the bone be removed, without removing excessive bone. The prior adhesive may be removed using a rotary tool having a powered cutting end.

This procedure may be performed with the powered cutting end of the rotary tool submersed within an irrigation fluid for removing heat from the bone tissue to prevent bone necrosis. Cuttings from the bone and adhesive are suspended as particulates in the irrigation fluid, making it difficult for a surgeon to visually inspect the area of the specimen to determine when the prior adhesive has been removed and obstructing inspection of the bone interior being resected.

SUMMARY OF THE INVENTION

A surgical tool and method for operating the surgical tool are provided for resecting bone. The surgical tool includes a pneumatic motor to which a bearing tube is secured for rotatably supporting a resecting tool. The bearing tube is eccentrically disposed within an attachment tube, with a flow channel defined between an interior of the attachment tube and an exterior of the bearing tube. Irrigation fluid is passed through the flow channel to maintain a constant flow of irrigation fluid about a cutting end of the resecting tool. Optical fibers extend within the attachment tube for passing light to lenses disposed at the specimen end of the attachment tube for providing illumination. At least one optical fiber extends from a lens at the specimen end, through the attachment tube, and to an optical viewer for providing a means for inspecting the bone being resected. The attachment tube is slidably adjustable along the bearing tube for selecting a distance between the specimen end of the attachment tube and the cutting end of the resecting tool.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

FIG. 1 is a perspective view which schematically depicts a surgical tool of the present invention for resecting bone to remove adhesive therefrom;

FIG. 2 is a sectional view taken along section line 2—2 of FIG. 1;

DETAILED DESCRIPTION OF THE PREFERRED EMBODIMENT

Figure 3:
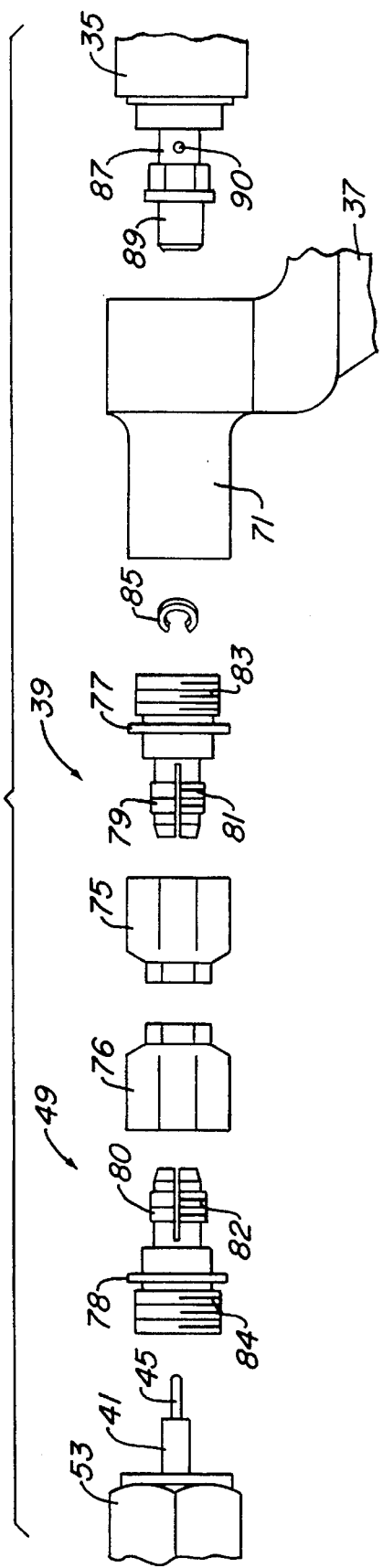
FIG. 3 is an exploded view depicting two compression assemblies, the first for slidably securing the bearing tube to the pneumatic motor and the second for slidably securing the attachment tube to the bearing tube.

FIG. 1 is a perspective view which schematically depicts surgical tool 11 of the present invention for resecting bone 13 to remove adhesive 15 therefrom. As depicted, surgical tool 11 is used within pool 16 of an irrigation fluid, such as water 17 which may be enclosed within elastomeric dam 19. Water 17 removes heat to prevent bone necrosis. Suction device 21 is selectively connected to flow tube 22 for drawing irrigation fluid 17 into flow tube 22 to remove irrigation fluid 17 from pool 16. Water supply 23 is selectively connected to flow tube 24 and provides water 17. Optical viewer 25 and light receptor 27 provide a means by which a surgeon may view the interior of bone 13 which is being resected to remove adhesive 15 therefrom. Optical viewer 25 includes a monitor for viewing the resecting procedure. Light receptor 25 provides a light source for use to illuminate the interior of bone 13. In this embodiment of the present invention, light receptor 27 picks up ambient light, but in other embodiments of the present invention, optical viewer 25 may include an internal light source for providing illumination for surgical tool 11.

Air supply 29 is connected to hose 31. Hose 31 includes concentric tubes, with an interior tube providing an air supply for powering surgical tool 11, and an annular space defined between the interior and exterior tubes providing a return flowpath for air exhausted from surgical tool 11. Connector 33 is provided to connect hose 31 to pneumatic motor 35. Pistol-grip handle 37 provides a handle for controlling the positioning of surgical tool 11. Pneumatic motor 35 is rigidly secured to pistol-grip handle 37.

First compression assembly 39 is provided for securing bearing tube 41 to pistol-grip handle 37 and pneumatic motor 35. Resecting tool 43 extends from pneumatic motor 35 and through bearing tube 41. Resecting tool 43 includes shank 45 which secures to pneumatic motor 35 and extends into cutting tool 47. In the preferred embodiment of the present invention, cutting tool 47 is formed on the end of shank 45.

Second compression assembly 49 is provided for slidably securing attachment tube 51 exteriorly about bearing tube 41. Attachment tube 51 includes connector 53, which provides a means for passing optical fibers 55 interiorly into attachment tube 51, and a means for passing irrigation fluid between flow port 57 and attachment tube 51. In the preferred embodiment, irrigation fluid passes through flow port 57 and into attachment tube 51.

FIG. 2 is a sectional view taken along section line 2—2 of FIG. 1. Bearing tube 41 is shown eccentrically disposed within attachment tube 51. Bearing tube 41 provides a means for supporting shank 45. Flow channel 59 is defined between attachment tube 51 and bearing tube 41 for providing an irrigation fluid flow passage. Flow channel 59 is sized so that a sufficient flow of irrigation fluid may be passed interiorly therein for operation of surgical tool 11. In the preferred embodiment, the irrigation fluid flows from attachment tube 51 at a discharge port in a specimen end 60

(shown in FIG. 1) of attachment tube 51 at a flow rate which is sufficient for preventing entrapment of air within the irrigation fluid. Air entrapment within the irrigation fluid would result in reduced visibility, and thus prevent proper inspection of the interior of the specimen, bone 13, when operating surgical tool 11.

Optical fibers 55 include fibers 61, 63, 65, 67 and 69, which are provided within illumination and vision passages which longitudinally extend within attachment tube 51. Lenses 70 extend within specimen end 60 (shown in FIG. 1) of attachment tube 51 to provide a means for disbursing and collecting light for passing an optical signal to and from optical fibers 61, 63, 65, 67 and 69. Optical fibers 61, 63, 65, 67 and 69 extend within attachment tube 51 so that tube 51 provides a round, tubular surface for circumferentially sealing within a cannula. Thus, the present invention may be used in surgical operations which require a seal between attachment tube 51 and a cannula for sealing against loss of gases or fluids, yet which may also require extension and rotation of attachment tube 51 within the cannula.

In this embodiment of the present invention, optical fibers 61, 63, 65, 67 and 69 can be connected to optical viewer 25 in different configurations, such as for providing either monovision or stereovision viewing modes. In the monovision viewing mode, optical fiber 65 is used for passing light to optical viewer 25 for optical inspection of bone 13 and adhesive 15 (shown in FIG. 1), and optical fibers 61, 63, 67 and 69 are provided for illuminating the interior of bone 13. In the stereo viewing mode, optical fibers 63 and 67 are provided for passing light to optical viewer 25 for viewing the surgical procedure, and optical fibers 61, 65 and 69 will pass light interiorly into the specimen for illumination. It should be noted than in other embodiments of the present invention, other configurations of optical fibers are possible.

FIG. 3 is an exploded view depicting compression assemblies 49 and 39, which are used for securing pneumatic motor 35 to bearing tube 41, and attachment tube 51 to bearing tube 41. Compression assemblies 39 and 49 include collet nuts 75 and 76, and collet rings 77 and 78. Slits in collet rings 77 and 78 provide longitudinally extending collets 79 and 80. Threads 81 and 82 are provided for securing collet nuts 75 and 76 to collet rings 77 and 78, respectively. Threads 83 are provided for securing collet ring 77 within coupling 71 of handle 37, to which motor 35 is secured. Threads 84 secure collet ring 78 within connector 53 to secure attachment tube 51 to bearing tube 41. Snap ring 85 fits within a groove interiorly machined into the end of collet ring 77 beneath threads 83, and acts as a stop to prevent bearing tube 41 from sliding into drive shaft 87 of pneumatic motor 35. Collet nuts 75 and 76 include interior threads for securing to threads 81 and 82, and when tightened swedge collets 79 and 80 inward to grip bearing tube 41 to rigidly secure bearing tube 41 therein.

Shank 45 is secured to drive shaft 87 by chuck 89. Hole 90 extends through drive shaft 87 for receipt of a pin to provide a means for holding and preventing rotation of drive shaft 87 as chuck 89 is loosened and tightened for selectively securing shank 45 therein. Coupling 71 is threadingly secured to motor 35 and collet ring 77 for rigidly securing bearing tube 41 to motor 35.

Operation of surgical tool 11 of the present invention is now described in reference to FIGS. 1 through 3. Resecting tool 43 is selected for insertion through bearing tube 41 and into chuck 89, which secures shank 45 to drive shaft 87 of motor 35. Bearing tube 41 is then secured within first compression assembly 39 to select a length between the end of bearing tube 41, which is opposite of motor 35, and cutting tool 47. Then, first compression assembly 39 is tightened to rigidly secure bearing tube 41 to pneumatic motor 35.

End 60 of attachment tube 51, which is opposite motor 35, is then selectively moved with respect to cutting tool 47 to select a distance therebetween. This distance is optimally selected depending on the depth of vision and field of view provided by lenses 70. Once the distance for optimally viewing the resecting procedure is selected, second compression assembly 49 is tightened to rigidly secure attachment tube 51 to bearing tube 41, which is rigidly secured to motor 35 and handle 37 by compression assembly 39.

Water supply 23 is selectively connected to flow tube 24 for passing water to flow port 57, and suction 21 is selectively connected to flow tube 22 for drawing water from within pool 16. Water supply 23 is then operated to provide pool 16 of water 17 by pumping irrigation fluid through irrigation port 57 and flow channel 59, and through a discharge port at specimen end 60 of attachment tube 51. Light receptor 27 is placed for receiving light to provide a light source for illuminating the specimen during resection. Once an adequate amount of irrigation fluid is passed interiorly into elastomeric dam 19 to provide pool of water 17, suction device 21 may be selectively operated to remove irrigation fluid 17 therefrom.

Air is then passed through hose 31 to motor 35 and back therethrough for driving motor 35, which rotates resecting tool 43 to remove adhesive 15 from the interior of bone 13. An optical signal is displayed on a view screen of optical viewer 25 to allow a surgeon to visually inspect and monitor cutting tool 47, adhesive 15 and the interior of bone 13. Thus, the surgeon can determine where to direct cutting tool 47 for removing adhesive 15 and avoiding removal of bone 13.

Referring again to FIG. 1, surgical tool 11 may be provided with optional valve means 91 through 94 (shown in phantom) for selectively coupling suction 21 and water supply 23 to opposite ones of flow tubes 22, 24 by means of optional flow lines 95 and 96 (shown in phantom). Thus, valve means 91 and 94 may be operated to selectively apply suction to flow line 95, flow tube 24 and flow port 57 for drawing irrigation fluid from pool 16 and through flow channel 59 (shown in FIG. 2). Then, valve means 92 and 93 should be selectively operated so that water supply 23 is connected to flow line 96 and flow tube 22 for providing irrigation fluid to supply pool 16. It should also be noted that it is preferable to isolate each of suction 21 and water supply 23 from connection to the one of flow tubes 22 and 24 to which the other of suction 21 and water supply 23 is connected. Further, valve means 91 through 94, flow line 95, and flow line 96 are optional since suction 21 and water supply 23 may be directly connected to the appropriate ones of flow tubes 23 and 24.

Figure 4:
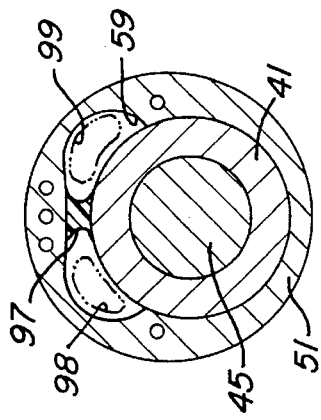
FIG. 4 is a sectional view taken along section lines 2—2 of FIG. 1, and depicts an alternative embodiment of the surgical tool for the present invention.

Referring to FIG. 4, an alternative embodiment to surgical tool 11 of the present invention is depicted. Seal member 97 provides a hydraulic seal in flow channel 59, between bearing tube 41 and attachment tube 51, to separate flow channel 59 into two separate flow channels. In this alternative embodiment, suction 21 and water supply 23 (show in FIG. 1) may be simultaneously applied to flow channel 57, rather than providing a separate flow tube 22 (shown in FIG. 1). A second flow port, similar to flow port 57, would then be required for connecting to flow channel 59. Further, separate flow tubes 98 and 99 (shown in phantom) may be provided for simultaneously providing suction 21 and irrigation fluid from water supply 23 through a flow channel 57 with an attachment tube 51. Then, seal 97 is optional and not required.

When suction and supply irrigation fluids are selectively passed through an attachment tube of the present invention, one of either the inlet port for suction or the discharge port for supply irrigation fluid may be positioned distal from an end 60 of attachment tube 51, such as at point 100 (shown in FIG. 1). To provide a port which is distal from end 60, such as at point 100, a drill hole may be provided to extend through the side of attachment tube 51 and connect into an appropriate portion of flow channel 59.

The present invention provides several advantages over prior art surgical tools for resecting bone. Optical fibers and lenses are included in the surgical tool of the present invention for directing light through the surgical tool. The optical fibers may be selectively connected for providing either stereo or monovision. In the preferred embodiment, several optical fibers direct light to lenses for illuminating the interior of the bone being resected, and one optical fiber directs light from a lens to an optical viewer for remotely monitoring the procedure. Additionally, the surgical tool of the present invention is selectively adjustable to accommodate a particular depth of vision and field of view for optical lenses.

A flow of irrigation fluid is passed through the surgical tool and across the cutting end of the resecting tool for removing heat to prevent bone necrosis. The irrigation fluid flow also passes across optical lenses in the end of the surgical tool to remove debris from the lenses which would obstruct illumination and vision. The irrigation fluid flow also displaces irrigation fluid having particulate matter suspended therein to further prevent obstruction of illumination and vision. The rate of flow for the irrigation fluid passing through the surgical tool is selected to provide sufficient flow for preventing bone necrosis and obstruction of illumination and vision, yet is sufficiently slow so that air will not become entrapped within the irrigation fluid. The irrigation fluid flow through the surgical tool may be provided by either passing a supply of irrigation fluid through the surgical tool to discharge at the specimen end of the tool, applying suction to the surgical tool and drawing irrigation fluid from around the bone into the surgical tool, or both.

The optical fibers and irrigation fluid flow channel extend within a single outer attachment tube. The outer attachment tube has a circular periphery to allow a circumferential seal. This allows a surgical tool according to the present invention to be used within a cannula to provide a fluid seal for preventing passage of gases and liquids, while allowing rotational and axial movement within the cannula.

Although the invention has been described with reference to a specific embodiment, this description is not meant to be construed in a limiting sense. Various modifications of the disclosed embodiment as well as alternative embodiments of the invention will become apparent to persons skilled in the art upon reference to the description of the invention. It is therefore contemplated that the appended claims will cover any such modifications or embodiments that fall within the true scope of the invention.

We claim:

1. In a surgical tool for resecting a bone interior of the type having a tool motor from which a drive shaft extends, a resecting tool which includes a shank for securing to the drive shaft of the tool motor and a cutting tool disposed at an end of the shank which is distal from the tool motor and rotatably driven by the tool motor, and a tool guide extending from the motor to a specimen end of the tool guide, which is distal from the tool motor, the tool guide including a bearing passage which extends therein between the motor and the specimen end for rotatably supporting the shank for turning with the drive shaft to rotate the cutting tool, the improvement comprising:

an attachment tube having two eccentric and overlapping bores extending longitudinally through the attachment tube;

the tool guide being disposed in a first one of the bores through the attachment tube;

the second one of the bores and an exterior portion of the tool guide defining a fluid channel which extends between an intake port and a discharge port for passing fluid between the intake port and the discharge port, wherein one of the intake and discharge ports is disposed proximate to the specimen end of the tool guide; and means for receiving light from about the cutting tool, and directing the light along the tool guide and to an optical viewer for visually inspecting the bone interior being resected.

2. The surgical tool according to claim 1, further comprising:

means for passing illumination light to a position proximate to the specimen end of the tool guide, and dispersing the illumination light about the cutting tool to illuminate the bone interior being resected.

3. The surgical tool according to claim 1, further comprising:

means for rigidly securing the tool guide to a stationary portion of the tool motor, said means for rigidly securing being selectively releasable to allow the tool guide to move relative to the resecting tool to select a distance between the cutting tool and the specimen end of the tool guide.

4. The surgical tool according to claim 1, further comprising:

means for passing illumination light to a position proximate to the specimen end of the tool guide, and dispersing the illumination light about the cutting tool to illuminate the bone interior being resected; and means for rigidly securing at least part of the tool guide to a stationary portion of the tool motor, said means for rigidly securing being selectively releasable to allow the tool guide to move relative to the resecting tool to select a distance between the cutting tool and the specimen end of the tool guide.

5. The surgical tool according to claim 1, wherein the means for receiving and directing the light comprises:

two lenses disposed proximate to the specimen end of the attachment tube for receiving light from about the cutting tool and portion of the bone interior being resected, and focusing the light into linear directions;

two optical fibers extending within the attachment tube, the optical fibers having ends disposed proximate to a separate one of the two lenses for receiving the light focused by the lenses and directing the light from the lenses, through the attachment tube and to the optical viewer; and the optical viewer, being operable in a stereo vision viewing mode.

6. The surgical tool according to claim 1, wherein:

means for separating the fluid channel of the second one of the bores into two separate fluid flow passages for simultaneously passing an irrigation fluid in two opposite directions within the fluid channel.

7. The surgical tool according to claim 1, wherein:
a third bore which is eccentric with and overlaps the two bores.

8. The surgical tool according to claim 1, wherein:
the tool guide is eccentrically disposed within the attachment tube.

9. The surgical tool according to claim 1, wherein:
two lenses disposed proximate to the specimen end of the attachment tube for receiving light from about the cutting tool and portion of the bone interior being resected, and focusing the light into linear directions; and two optical fibers extending within the attachment tube, the optical fibers having ends disposed proximate to a separate one of the two lenses for receiving the light focused by the lenses, and directing the light from the lenses, through the attachment tube and to the optical viewer;

the optical viewer, being operable in a stereo vision viewing mode;

means for directing illumination light to a position proximate to the specimen end of the tool guide, and dispersing the illumination light about the cutting tool to illuminate the bone interior being resected; and means for rigidly securing the tool guide to a stationary portion of the tool motor, said means for rigidly securing being selectively releasable to allow the tool guide to move relative to the resecting tool to select a distance between the cutting tool and the specimen end of the tool guide.

10. A surgical tool for resecting an adhesive from a bone interior, the surgical tool comprising in combination:
a tool motor having a drive shaft;

a resecting tool having a shank for securing to the drive shaft of the tool motor, and a cutting tool disposed at an end of the shank which is distal from the tool motor and rotatably driven by the tool motor;

a bearing tube through which the resecting tool extends, rotatably supported by the bearing tube, the bearing tube being rigidly secured to a stationary portion of the tool motor;

an attachment tube having a central passage for slidably securing the bearing tube therein for selectably telescoping the attachment tube along the bearing tube, and an irrigation fluid flow channel extending within the attachment tube for passing an irrigation fluid between an intake port and a discharge port, wherein one of the intake and discharge ports are disposed proximate to a specimen end of the attachment tube;

a first optical fiber extending from a light source, through the attachment tube and to the specimen end of the attachment tube for passing light from the light source to the specimen end of the attachment tube;

a first lens disposed proximate to the specimen end of the attachment tube for receiving the light from the first optical fiber and dispersing the light to illuminate the bone interior disposed about the cutting tool;

a second lens disposed proximate to the specimen end of the attachment tube for receiving the light from about the cutting tool, and focusing the light into a linear direction within the attachment tube;

a second optical fiber extending within the attachment tube for receiving the light from the second lens, and passing the light to an optical viewer; and wherein the bearing tube is rigidly secured within the attachment tube by a compression assembly, which includes a collet ring having collets extending longitudinally therefrom, and a collet nut for threadingly securing to the collet ring and turning thereon to squeeze the collets between the collet nut and an exterior surface of the bearing tube to rigidly secure the bearing tube within the attachment tube.

11. The surgical tool according to claim 10, further comprising:
an optical viewer which is operable in a stereo vision viewing mode;

a third lens, spaced apart from the second lens, and disposed proximate to the specimen end of the attachment tube for receiving light from about the cutting tool, and focusing the light into the attachment tube;

a third optical fiber extending within the attachment tube for receiving the light from the third lens and passing the light to the optical viewer; and wherein the light of the second and third optical fibers is directed to the optical viewer for viewing the bone interior in a stereo vision viewing mode.

12. The surgical tool according to claim 10, further comprising:
attachment means for rigidly securing the bearing tube to the tool motor, releasing for moving the bearing tube over the shank of the resecting tool to determine a distance between the cutting tool and the end of the bearing tube which is distal from the tool motor, and then rigidly securing the bearing tube to a stationary portion of the tool motor with the distance fixed between the end of the bearing tube and the cutting tool.

13. The surgical tool according to claim 10, wherein the attachment means comprises:
a first collet ring having first threads for securing to the tool motor, and first collets which longitudinally extend therefrom along a first exterior portion of the bearing tube; and a first collet nut threadingly secured to the first collet ring for urging the first collets to squeeze between an interior of the first collet nut and the first exterior portion of the bearing tube to selectively secure the bearing tube to the tool motors.

14. The surgical tool according to claim 10, wherein the bearing tube is eccentrically secured within the attachment tube.

15. The surgical tool according to claim 10, further comprising:
a third lens disposed proximate to the specimen end of the attachment tube for receiving the light from about the cutting tool, and focusing the light into the attachment tube;

an optical viewer which is operable in a stereo vision viewing mode;

a third optical fiber extending within the attachment tube for receiving the light from the third lens, and passing the light to an optical viewer;

attachment means for rigidly securing the bearing tube to a stationary portion of the tool motor, and being releasible for selectively moving the bearing tube over the shank of the resecting tool to determine a distance between the cutting tool and the end of the bearing tube which is distal from the tool motor, and then being securable to secure the bearing tube to the stationary portion of the tool motor with the distance fixed between the end of the bearing tube and the cutting tool; and wherein the bearing tube is eccentrically secured within the attachment tube.

16. A surgical tool for resecting an adhesive from a bone interior, the surgical tool comprising in combination:

a tool motor having a drive shaft;

a resecting tool having an elongated shank for securing to the drive shaft of the tool motor, and a cutting tool disposed at an end of the shank which is distal from the tool motor and rotatably driven by the tool motor;

a bearing tube having a fixed length, rigidly secured to a stationary portion of the tool motor and having a bearing passage through which the resecting tool extends, rotatably supported by the bearing tube;

an attachment tube having a fixed length, a central passage for slidably securing the bearing tube therein for selectably moving the attachment tube along the bearing tube, and a fluid flow channel extending within the attachment tube for passing an irrigation fluid between an intake port and a discharge port, wherein one of the intake and discharge ports is disposed proximate to a specimen end of the attachment tube;

first attachment means for rigidly securing the bearing tube within the attachment tube, and which is releasible for selectively moving the attachment tube over the bearing tube to determine a length between the cutting tool and the specimen end of the attachment tube;

a first optical fiber extending within the attachment tube from a light source to a point which is proximate to the specimen end of the attachment tube for passing light therethrough;

an optical viewer;

a first lens disposed about the specimen end of the attachment tube for receiving the light from the first optical fiber and dispersing the light to illuminate the bone interior disposed about the cutting tool;

a second optical fiber extending within the attachment tube to a second point which is proximate to the specimen end of the attachment tube for passing at least a portion of the light through the attachment tube; and a second lens disposed proximate to the specimen end of the attachment tube for receiving light from around the cutting tool and directing the light into the second optical fiber for passing to the optical viewer.

17. The surgical tool according to claim 16, further comprising:

a third lens disposed about the specimen end of the attachment tube for receiving the light from about the cutting tool, and directing the light into the attachment tube;

a third optical fiber extending within the attachment tube for receiving the light from the third lens and passing the light through the attachment tube and to the optical viewer; and wherein the optical viewer is operable in a stereo vision viewing mode.

18. The surgical tool according to claim 16, wherein;

the central passage and the fluid flow channel of the attachment tube are defined by at least two eccentric and overlapping bores;

the bearing tube is disposed within a first one of the at least two bores which define the central passage of the attachment tube; and the fluid flow channel is defined within a second one of the at least two bores, between an interior surface of the attachment tube and an exterior surface of the bearing tube.

19. The surgical tool according to claim 16, further comprising:

a third lens disposed proximate to the specimen end of the attachment tube for receiving the light from about the cutting tool, and directing the light into the attachment tube;

a third optical fiber extending within the attachment tube for receiving the light from the third lens and passing the light to the optical viewer;

wherein the optical viewer is operable in a stereo vision viewing mode;

wherein the central passage of the attachment tube is defined by at least two eccentric and overlapping bores;

wherein the bearing tube is disposed within a first one of the two bores of the central passage of the attachment tube; and wherein the fluid flow channel is defined within a second one of the two bores of the central passage, between an interior surface of the attachment tube and an exterior surface of the bearing tube.

20. The surgical tool according to claim 16, further comprising:

the central passage of the attachment tube being defined by three eccentric and overlapping bores formed into the attachment tube;

wherein the bearing tube is disposed within a first one of the three bores of the central passage of the attachment tube; and fluid seal means extending within the second and third bores, separating the fluid flow channel into two separate fluid flow passages for simultaneously passing fluid in opposite directions within the central passage of the attachment tube.

21. The surgical tool according to claim 16, further comprising:

a third lens disposed proximate to the specimen end of the attachment tube for receiving the light from about the cutting tool, and directing the light into the attachment tube;

a third optical fiber extending within the attachment tube for receiving the light from the third lens and passing the light to the optical viewer;

wherein the optical viewer is operable in a steriovision viewing mode;

the central passage of the attachment tube being defined by three eccentric and overlapping bores formed into the attachment tube;

wherein the bearing tube is disposed within a first one of the three bores of the central passage of the attachment tube; and fluid seal means extending within the second and third bores, separating the fluid flow channel into two separate fluid flow passages for simultaneously passing fluid in opposite directions within the central passage of the attachment tube.

22. A method for resecting a specimen with a surgical tool having a tool motor for rotating a drive shaft, and a resecting tool secured to the drive shaft for rotating therewith to turn a cutting tool defined by an end of the resecting tool, the method comprising the steps of:

providing a tool guide for rigidly securing to a stationary portion of the tool motor, the tool guide having a bearing passage and an irrigation fluid flow passage extending longitudinally therein to a specimen end of the tool guide which is proximate to the cutting tool;

providing a first, second and third lenses mounted to the specimen end of the tool guide, with at least the second and third lenses being moveable relative to the tool motor for selecting mounting distances therebetween;

providing first, second and third optical fibers extending within the tool guide for passing light through the tool guide to the first lens for dispersing light about the cutting tool and directing part of the light from about the cutting tool, longitudinally through the tool guide and to an optical viewer;

providing the resecting tool with a shank for rotatably securing within the bearing passage of the tool guide;

providing an optical viewer which is operable in a stereo vision viewing mode;

securing the shank of the resecting tool within the bearing passage, rotatably supported within the bearing passage for rotating with the drive shaft;

rigidly securing at least part of the tool guide to a stationary portion of the tool motor;

moving the second and third lenses relative to the tool motor to determine selected distances between the second and third lenses and the cutting tool;

rigidly securing the second and third lenses to the stationary portion of the tool motor, at the selected distances from the cutting tool;

rotating the resection tool to resect the specimen;

passing an irrigation fluid through the irrigation fluid flow passage and the specimen end of the tool guide, proximate to the cutting tool;

directing the light through the first optical fiber and the first lens, dispersing the light about the cutting tool;

receiving at least part of the light into the second and third lenses, and then focusing the light into the second and third optical fibers, respectively; then directing the part of the light through the tool guide and to an optical viewer for displaying the specimen in a stereo vision viewing mode.

23. The method according to claim 22, wherein the step of passing the irrigation fluid through the irrigation fluid flow passage comprises:

selectively applying suction to the irrigation fluid flow passage;

drawing the irrigation fluid into the specimen end of the tool guide; and then passing the irrigation fluid through the irrigation fluid flow passage.

24. The method according to claim 22, further comprising the step of:

providing two separate flow channels within the irrigation fluid flow passage;

passing a first portion of the irrigation fluid through a first one of the two flow channels and from the specimen end of the tool guide, proximate to the cutting tool; and drawing a second portion of the irrigation fluid into a second one of the two flow channels and passing the second portion of the irrigation fluid through the tool guide in a direction which is opposite to the flow of the first portion of the irrigation fluid passing within the first one of the two flow channels.

25. The method according to claim 22, wherein the tool guide is provided to include a bearing tube and an attachment tube which are releasably secured together, and the second and third lenses and second and third optical fibers extend within the attachment tube, wherein the steps of moving the second and third lenses relative to the tool motor and rigidly securing the second and third lenses to the stationary portion of the tool motor comprise:

sliding the attachment tube along the bearing tube to determine the selected distances between a specimen end of the attachment tube and the cutting tool to accommodate a particular field of view for the second and third ones of the lenses; and securing the attachment tube to the bearing tube to rigidly secure attachment tube to the motor, and retain the selected distances between the cutting tool and the at least one of the lenses.

26. The method according to claim 22, wherein the tool guide is provided to include a bearing tube and an attachment tube which are releasably secured together, the bearing tube is releasably secured to the tool motor, and the second and third lenses and second and third optical fibers extend within the attachment tube, the method further comprises the steps of:

sliding the bearing tube along the shank of the resecting tool to determine a first distance between the cutting tool and the bearing tube, and second distance between the motor and the bearing tube;

rigidly securing the bearing tube to a stationary portion of the motor, with the bearing tube rotatably supporting the shank of the resecting tool for rotation with the drive shaft of the motor;

sliding the attachment tube along the bearing tube to determine the selected distances between a specimen end of the attachment tube and the cutting tool to accommodate a particular field of view for the second and third ones of the lenses; and rigidly securing the attachment tube to the bearing tube for rigidly securing attachment tube to the motor, and retaining the lineal distances between the cutting tool and the second and third lenses.

* * * * *